(12) United States Patent
Chen

(10) Patent No.: US 8,222,268 B2
(45) Date of Patent: *Jul. 17, 2012

(54) METHODS FOR REDUCING VEIN IRRITATION

(75) Inventor: Andrew Xian Chen, San Diego, CA (US)

(73) Assignee: Adventrx Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/212,140

(22) Filed: Aug. 17, 2011

(65) Prior Publication Data

US 2012/0046310 A1  Feb. 23, 2012

Related U.S. Application Data

(63) Continuation of application No. 12/965,676, filed on Dec. 10, 2010, now Pat. No. 8,026,250, which is a continuation of application No. 10/889,226, filed on Jul. 12, 2004, now Pat. No. 7,871,632.

(51) Int. Cl.
*A01N 43/42* (2006.01)
*A61K 31/44* (2006.01)
*A61K 9/00* (2006.01)

(52) U.S. Cl. ........................ 514/283; 424/400

(58) Field of Classification Search .................. None
See application file for complete search history.

(56) References Cited

U.S. PATENT DOCUMENTS

| | | | |
|---|---|---|---|
| 4,816,247 A | 3/1989 | Desai et al. | |
| 5,399,363 A | 3/1995 | Liversidge et al. | |
| 5,576,016 A | 11/1996 | Amselem et al. | |
| 5,977,172 A | 11/1999 | Yoshikawa et al. | |
| 6,383,471 B1 | 5/2002 | Chen et al. | |
| 6,720,001 B2 | 4/2004 | Chen et al. | |
| 6,723,338 B1 | 4/2004 | Sarris et al. | |
| 2001/0039289 A1 | 11/2001 | Blok et al. | |
| 2003/0224042 A1 | 12/2003 | Bougaret et al. | |

FOREIGN PATENT DOCUMENTS

| | | |
|---|---|---|
| JP | 2003-277281 | 10/2003 |
| WO | WO 90/14094 A1 | 11/1990 |
| WO | WO 01/30351 A1 | 5/2001 |

OTHER PUBLICATIONS

Berge, Stephen M., et al.; Pharmaceutical Salts; Journal of Pharmaceutical Sciences; vol. 66, No. 1; pp. 1-19; Jan. 1977.
"Prescribing Information—NAVELBINE® (vinorelbine tartrate) Injection," Manufactured by Pierre Fabre Médicament Production, 64320 Idron, France, GlaxoSmithKline, Previously presented. Nov. 1-17, 2002.
Wang et al.; Venous Irritation, Pharmacokinetics, and Tissue Distribution of Tirilazad in Rats Following Intravenous Administration of a Novel Supersaturated Submicron Lipid Emulsion; *Pharmaceutical Research*; (1999) vol. 16, No. 6.
Von Dardel, et al.; Diazepam in Emulsion Form for Intravenous Usage; *Acta Anasth.Scand.*; (1976) 20, 221-224.

*Primary Examiner* — David J Blanchard
*Assistant Examiner* — Trevor Love
(74) *Attorney, Agent, or Firm* — Kilpatrick Townsend & Stockton LLP

(57) ABSTRACT

The present invention provides compositions for delivering highly water-soluble drugs (such as vinca alkaloids) and methods of using such compositions.

16 Claims, 2 Drawing Sheets

METHODS FOR REDUCING VEIN IRRITATION

CROSS-REFERENCE TO RELATED APPLICATIONS

This application is a continuation of U.S. application Ser. No. 12/965,676, filed on Dec. 10, 2010, which is now U.S. Pat. No. 8,026,250, which application is a continuation of U.S. application Ser. No. 10/889,226, filed on Jul. 12, 2004, which is now U.S. Pat. No. 7,871,632.

BACKGROUND OF THE INVENTION

1. Field of the Invention

This invention relates to an emulsion composition for delivering highly water-soluble drugs such as vinca alkaloids.

2. Description of the Related Art

Despite years of research into the development of more effective and safe therapeutic agents for cancer, cancer drugs remain extremely toxic to patients. The common systemic toxicities associated with cancer drugs, such as chemotherapeutic agents, include bone marrow suppression, asthenia, peripheral neuropathy, dyspnea, alopecia, etc. To make things worse, many intravenously injected cancer drugs can cause local reactions at the injection site resulting in vein irritation, pain, tissue necrosis and/or thrombophlebitis. The consequence of injection site reactions to a chemotherapy agent may include extreme pain, early termination of drug treatment, wounds that are difficult to heal, scars, permanent tissue damage, and, in the worst case, amputation.

Alkaloids isolated from the periwinkle plant (*Vinca rosea*) and derivatives thereof, collectively referred to as "vinca alkaloids," have proven effective as first line therapy for many types of lymphomas, leukemias, and other cancers. Vincristine and vinblastine consist of a catharanthine moiety linked to vindoline, and the structures differ by a single substitution in the vindoline group. Vindesine, a desacetyl carboxyamide derivative of vinblastine, was synthesized later. Subsequently, novel synthetic approaches were used to generate compounds that differed from the natural compounds by the presence of an eight-rather than a nine-member catharanthine ring, including vinorelbine, which is commonly available as a tartrate salt, i.e., vinorelbine bitartrate or vinorelbine tartrate.

Vinca alkaloids are highly cytotoxic drugs that disrupt microtubules, inhibit cell division and induce apoptosis. Without wishing to be bound to a particular theory, it is believed that vinca alkaloids exert their cytotoxic effects by binding to tubulin, the protein subunit of microtubules.

Vincristine, vinblastine and vinorelbine are the best-known members of this drug family and are widely used clinically. Despite having similar structures and mechanisms of action, vinca alkaloids differ in their antitumor activity and toxicities. For example, vincristine is used mostly to treat hematological cancer, and neurotoxicity is dose limiting. In contrast, vinorelbine is approved for the use as a single agent to treat breast and non-small cell lung cancer, and its injection site reaction is most severe amongst all vinca alkaloid drugs.

It is well known that all vinca alkaloid drugs are associated with adverse reactions at the injection site. For example, the current vinorelbine product approved in the U.S. (NAVELBINE®) has a "blackbox" warning due to its severe reaction at the injection site.

NAVELBINE® is reportedly associated with a high incidence (51%-61%) of local reactions at the injection site, characterized by injection site pain and phlebitis. The injection site reaction or extravasation of NAVELBINE® can be severe, ranging from considerable pain, irritation, and tissue necrosis to thrombophlebitis (The NAVELBINE® Product Information by GlaxoSmithKline).

NAVELBINE® (vinorelbine tartrate) is a simple solution formulation for intravenous administration. Each vial contains vinorelbine tartrate equivalent to 10 mg (1-mL vial) or 50 mg (5-mL vial) vinorelbine in water for injection at pH 3.5.

Rittenberg reported post-incident care and management of venous irritation or phelibitis due to NAVELBINE® (*Oncol. Nurs. Forum* 22: 707-10, 1995). Mare reported methods for preventing venous toxicity of NAVELBINE® by co-administering anti-inflammatory drugs as defibrotide or ketorolac, or changing infusion schedules from a bolus infusion to a slow infusion (*Support Care Cancer* 11: 593-6, 2003). However, the injection site toxicity problem of vinorelbine or other vinca alkaloids has not been properly addressed from the drug formulation approach and vinca alkaloid products remain the most venous toxic drugs.

Oil-in-water emulsion formulations may provide advantages over a traditional solution formulation such as the one used by NAVELBINE® in control of venous toxicity at injection site for irritating drugs. For example, the intramuscular or intravenous injection of erythromycin or clarithromycin in a solution formulation causes severe pain at the injection site, and erythromycin or clarithromycin fat emulsion (oil-in-water) is locally non-irritating (WO 90/14094). However, oil-in-water emulsion formulations are typically applied to only lipophilic drugs such as propofol, diazepam, erythromycin or clarithromycin, etc. Desai (U.S. Pat. No. 4,816,247) disclosed emulsion compositions for administration of sparingly water soluble ionizable hydrophobic drugs.

Without wishing to be bound to a particular theory, it is believed that in an oil-in-water emulsion, a lipophilic drug is preferentially dissolved in the oil phase and therefore is coated and/or encapsulated in the oil droplets, thus preventing direct contact of drug molecules at a high concentration with the venous endothelium tissue, thus reducing the venous toxicity of the drug.

However, to date, the utility of an emulsion in preventing venous toxicity of irritating drugs is limited to only lipophilic (or hydrophobic) drugs since highly water-soluble drugs, such as vinca alkaloid drugs, dol not partition well in the conventional emulsion oil droplets. For example, vinorelbine in the bitartrate salt form is highly soluble in water with an aqueous solubility is >1000 mg/mL in distilled water.

Thus, there remains a need in the art for developing compositions for delivering highly water soluble drugs. The present invention fulfills such a need and provides other related advantages.

BRIEF SUMMARY OF THE INVENTION

The present invention provides compositions for delivering highly water soluble drugs and methods for using such compositions.

In one aspect, the present invention provides compositions for delivering highly water soluble drugs that comprises a triglyceride oil, an emulsifier, a stabilizer, and water, wherein the composition is an emulsion having an oil and an aqueous phase, and the drug is substantially in the oil phase.

In certain embodiments, the highly water soluble drug is venous toxic and/or weakly basic absent the emulsion. In certain embodiments, the drug is selected from the group consisting of dopamine, ciprofloxacin, vancomycin, norvancomycin, doxorubicin, daunorubicin, vinca alkaloids (e.g., vinorelbine), and pharmaceutically acceptable salts thereof.

In certain embodiments, the triglyceride oil is a triglyceride having long chain fatty acids, a triglyceride having medium chain fatty acids, or a mixture thereof.

In certain embodiments, the emulsifier is egg lecithin, soy lecithin, a synthetic phospholipid, or a mixture thereof.

In certain embodiments, the stabilizer is a fatty acid (e.g., oleic acid), riboflavin-5-phosphate, vitamin-E succinate, cholesterol sulfate, or a mixture thereof.

In certain embodiments, the drug has an aqueous solubility of at least or over 30, 50, 75, 100, 125, 150, 175, 200, 250, 300, 350, 400, 450, 500, 550, 600, 650, 700, 750, 800, 850, 900, 950, or 1000 mg/ml.

In certain embodiments, the charge ratio of the drug and the stabilizer is 1:1 to 1:10. In certain embodiments, the charge ratio of the drug and the stabilizer is within the range of 5:1 to 3:1, 2:1 to 1:1, or 1.5:1 to 1:1.

In certain embodiments, no less than 80%, 85%, 90%, 92%, 94%, 95%, 96%, 97%, 98%, or 99% of the drug is present in the oil phase of the emulsion.

In certain embodiments, the drug in the emulsion composition is in a concentration range of about 1 to about 50 mg/ml. In certain embodiments, the concentration of the drug in the emulsion is about 2, 3, 4, 5, 6, 7, 8, 9, 10, 15, 20, 25, 30, 35, 40, 45 or 50 mg/ml.

In another aspect, the present invention provides a composition for delivering a highly water soluble, venous toxic and weakly basic drug that comprises an oil-in-solid dispersion prepared by freeze-drying the emulsion described herein.

In another aspect, the present invention provides a lyophilized formulation of a highly water soluble, venous toxic and weakly basic drug, wherein the formulation, when hydrated, produces the emulsion described herein.

In certain embodiments, when the lyophilized formulation is reconstituted in a liquid medium to provide particles, the particles increase in size by less than one-fold as compared to particles before lyophilization.

In another aspect, the present invention provides a method for treating cancer comprising administering to a patient in need thereof the compositions described herein wherein the drug in the composition is a vinca alkaloid (e.g., vinorelbine bitartrate). In certain embodiments, the composition is administered intravenously. In certain other embodiments, the composition is administered intramuscularly or intraarterially.

DETAILED DESCRIPTION OF THE INVENTION

Figure 1:
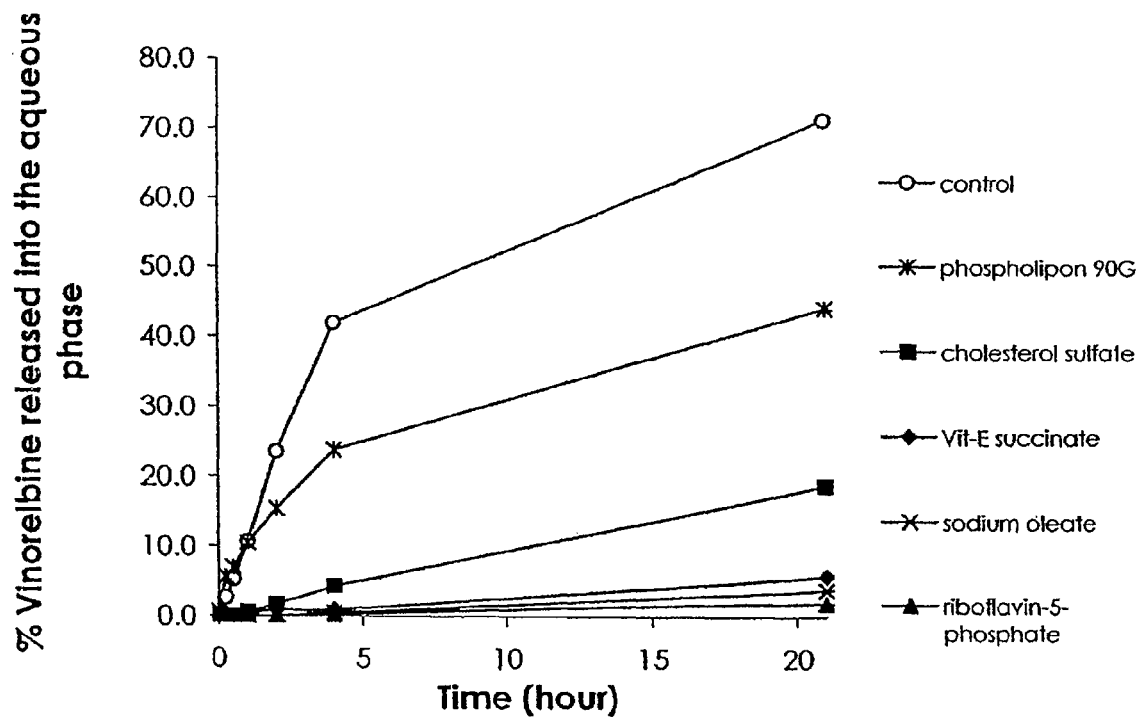
FIG. 1 shows the effects of various stabilizers on vinorelbine incorporation into the oil phase of an emulsion.

The present invention provides compositions for delivering highly water soluble drugs (including those that are also venous toxic and/or weakly basic). The pharmaceutical compositions are oil-in-water emulsions containing sub-micron size oil droplets, and comprise triglyceride oil, stabilizers, emulsifiers, and water. The compositions may optionally comprise preservatives and/or other inactive ingredients.

The term of "highly water-soluble drugs," as used herein, refers to a drug (in its freebase or salt form) having solubility in water in excess of 30 mg/ml at room temperature (20-25° C.). The solubility of a drug may be described in a variety of ways. The USP/NF generally expresses the solubility in terms of the volume of solvent required to dissolve 1 gram of the drug at a specified temperature (e.g., 1 g aspirin in 300 ml $H_2O$, 5 ml ethanol at 25° C.). Other references may use more subjective terms to describe solubility, such as those given in the following table from Remington's Pharmaceutical Sciences, Mack Publishing Co., Easton, Pa., latest edition.

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

Therefore, the "highly water-soluble drugs" of this invention include the drugs in the top 3 solubility categories, i.e., "very soluble," "freely soluble," and "soluble."

The term of "venous toxic drugs," as used herein, refers to drugs which, when intravenously injected in a solution formulation, can cause local reactions at the injection site that result in vein irritation, pain, tissue necrosis and/or thrombophlebitis.

The term "weakly basic drugs," as used herein, refers to drugs having at least one weakly basic functional group.

A "highly water-soluble, venous toxic and weakly basic drug" is commonly provided in a salt form. Examples of some commercial drugs, which fall into this category include, but are not limited to, dopamine hydrochloride, ciprofloxacin lactate, vancomycin hydrochloride, norvancomycin hydrochloride, doxorubicin hydrochloride, daunorubicin hydrochloride, vincristine sulfate, vindestin sulfate, vinblastine sulfate, and vinorelbine bitartrate.

In certain embodiments, the highly water-soluble drugs for use in this invention are anti-neoplastic agents.

In other embodiments, the highly water-soluble drugs for use in this invention are vinca alkaloids, and the pharmaceutically acceptable salts and derivatives thereof. Vinca alkaloids include, but are not limited to, vincristine, vinblastine, vindesine and vinorelbine.

In yet further embodiments, the highly water soluble drug for use in this invention is vinorelbine, and the pharmaceutically acceptable salts thereof.

Pharmaceutically acceptable salts," as used herein, refers to those salts which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of cancers. Among the more common pharmaceutically acceptable salts of vinca alkaloids are the tartrate, sulfate and hydrochloride forms. Other acid salts used in the pharmaceutical arts include adipate, acetate, bromide, mesylate, lactate, succinate, maleate, lactobionate, aspartate, benzoate, benzene sulfonate, bisulfate, butyrate, citrate, camphorate, camphorsulfonate, cyclopentanepropionate, digluconate, dodecylsulfate, ethanesulfonate, fumarate, gluconate, glycerophosphate, heptonate, hexanoate, hydrobromide, hydroiodide, 2-hydroxy ethanesulfonate, lactate, maleate, methanesulfonate, 2-naphthalenesulfonate, nicotinate, oxalate, pamoate, pantothenate, pectinate, persulfate, 3-phenylpropionate, picrate, pivalate, propionate, thiocyanate, tosylate, and undecanoate.

In certain embodiments, the vinorelbine salt is the bitartrate salt having a chemical name is 3',4'-didehydro-4'-deoxy-C'-norvincaleukoblastine [R-(R*,R*)-2,3-dihydroxybutanedioate (1:2) (salt)].

As used herein, the term "oil-in-water emulsion" refers to a colloidal dispersion systems in which liquid oil is dispersed in small droplets (the discrete phase) in an aqueous medium (the continuous phase), wherein in excess of 80% of the drug is dissolved and remains in the oil droplets. In certain embodiments, greater than 85%, 90%, 92%, 94%, 95%, 96%, 97%, 98%, or 99% of the drug is present in the oil phase:

As used herein, the term "an acidic pH" is meant the pH measured for the emulsion to be in the range of pH of 2 to 6. In certain embodiment, the emulsion has a pH of 3 to 5, pH 3 to 4, or pH 3.5 to 4.0.

As used herein, the term "sub-micron size droplet" is meant oil droplets in an oil-in-water emulsion having an average diameter of less than 1 micron as measured by conventional sizing techniques such as laser light scattering spectrometry. In certain embodiments, the oil droplets of the compositions of the present invention have an average diameter of less than 500, 450, 400, 350, 300, or 250 nm. Oil droplets of sub-micron size are desired for the safe passage of these droplets in the capillary blood vessel in the circulation. Droplets of greater than 5 micron in diameter are believed to be unsafe for intravenous injection since they may block the capillary vessel resulting in pulmonary embolism. In certain embodiments, the oil droplets of the compositions of the present invention have an average diameter of less than 0.2-micron (200 nm) so the emulsion may be sterilized by filtering through a 0.2 micron sized filter membrane.

In certain embodiments, the oil droplets of the compositions of the present invention have an average diameter of less than about 150, 100, 75, 50, 25, 20, 15, or 10 nm.

"Triglyceride oil," as used herein, refers to a triglyceride composition which is liquid at room temperature (20-25° C.), and which comprises primarily triglycerides of C6 to C18 fatty acids. Triglyceride oil is used in this invention to form the discrete phase of the emulsion or the oil droplets in which the drug is encapsulated. The triglyceride oil is thus desired to be non-toxic, biocompatible, and capable of forming stable droplets of the desired size and encapsulating the highly water-soluble drugs.

The triglyceride oil used in this invention can be glycerol esters of short chain (C4 to C6), medium chain (C8-C12), or long chain (C14 to C18) fatty acids or mixture thereof.

In certain embodiments, triglyceride oils of medium chain fatty acids may be used. Such oils comprise predominantly glycerol triesters of C8 to C12 fatty acids. These oils can be prepared synthetically by well-known techniques, or can be obtained from natural sources by known techniques of thermal or solvent fractionation of suitable natural oils, such as palm oil or coconut oil, to yield fractions rich in the desired low-melting triglycerides. An exemplary low-melting, low molecular weight triglyceride oil is a low molecular weight fraction of coconut or palm oil which is rich in mixed esters of caprylic (octanoic) and capric (decanoic) acids. Such oil is commercially available as Miglyol 812 from SASOL GmbH Germany, CRODAMOL GTCC-PN from Croda Inc. of Parsippany, N.J., or Neobees M-5 oil from PVO International, Inc., of Boonton, N.J. Other low-melting medium chain oils may also be used in the present invention.

In certain embodiments, triglyceride oils with a high percentage of glycerol triesters of unsaturated or polyunsaturated C14 to C18 fatty acids (long chain fatty acids) may be used. An example of such an oil is soybean oil, which typically has a fatty acid composition of about 80% oleic and linoleic acids. An injectable grade of soybean oil is commercially available as Super Refined USP grade oil from Croda Inc. of Parsippany, N.J. Another example of such an oil is safflower oil. Other low-melting vegetable oils or low-melting fractions of oils, including cottonseed, menhaden, olive, peanut, corn, sesame and flaxseed oil, which can be obtained by conventional thermal or solvent fractionation, may also be used in the present invention. While such unsaturated or polyunsaturated vegetable oils may offer a cost advantage in formulating compositions according to this invention, they also exhibit a greater tendency to oxidative deterioration, and may require the addition of oil soluble antioxidants, such as tocopherols.

The triglyceride oil is generally present in a range of from about 2 to about 40% in the final emulsion formulation. In certain embodiments, triglyceride oil is present at about 5%, 10%, 15%, 20%, 25%, 30%, or 35% by weight in the final emulsion formulation.

In certain embodiments, the triglyceride oil comprises a 1:1 weight ratio mixture of a medium chain triglyceride and a long chain triglyceride.

As used herein, the term "stabilizers" refers to those ingredients that retain the highly water-soluble drug in the oil droplets of an oil-in-water emulsion.

In other embodiments, the "stabilizers" comprise compounds selected from groups of fatty acids, cholesterol sulfate, riboflavin-5-phosphate, and vitamin E succinate or a mixture thereof.

Exemplary fatty acids include saturated fatty acids, monoenoic acids and polyenoic acids. The saturated fatty acids include, but are not limited to, those listed in the table below:

| Systematic name | Common name | Shorthand designation | Molecular wt. |
|---|---|---|---|
| butanoic | Butyric | 4:0 | 88.1 |
| pentanoic | Valeric | 5:0 | 102.1 |
| hexanoic | Caproic | 6:0 | 116.1 |
| octanoic | Caprylic | 8:0 | 144.2 |
| nonanoic | Pelargonic | 9:0 | 158.2 |
| decanoic | Capric | 10:0 | 172.3 |
| dodecanoic | Lauric | 12:0 | 200.3 |
| tetradecanoic | Myristic | 14:0 | 228.4 |
| hexadecanoic | Palmitic | 16:0 | 256.4 |
| heptadecanoic | margaric (daturic) | 17:0 | 270.4 |
| octadecanoic | Stearic | 18:0 | 284.4 |
| eicosanoic | Arachidic | 20:0 | 412.5 |
| docosanoic | Behenic | 22:0 | 340.5 |
| tetracosanoic | Lignoceric | 24:0 | 368.6 |
| hexacosanoic | Cerotic | 26:0 | 396.7 |
| heptacosanoic | Carboceric | 27:0 | 410.7 |
| octacosanoic | Montanic | 28:0 | 424.8 |
| triacontanoic | Melissic | 30:0 | 452.9 |
| dotriacontanoic | Lacceroic | 32:0 | 481 |
| tritriacontanoic | ceromelissic (psyllic) | 33:0 | 495 |
| tetratriacontanoic | Geddic | 34:0 | 509.1 |
| pentatriacontanoic | Ceroplastic | 35:0 | 523.1 |

Exemplary monoenoic fatty acids include those listed in the table below:

| Systematic name | Common name | Shorthand designation | Molecular wt. |
|---|---|---|---|
| cis-4-decenoic | Obtusilic | 10:1 (n-6) | 170.3 |
| cis-9-decenoic | Caproleic | 10:1 (n-1) | 170.3 |
| cis-5-lauroleic | Lauroleic | 12:1 (n-7) | 198.4 |

-continued

| Systematic name | Common name | Shorthand designation | Molecular wt. |
|---|---|---|---|
| cis-4-dodecenoic | Linderic | 12:1 (n-8) | 198.4 |
| cis-9-tetradecenoic | myristoleic | 14:1 (n-5) | 226.4 |
| cis-5-tetradecenoic | Physeteric | 14:1 (n-9) | 226.4 |
| cis-4-tetradecenoic | Tsuzuic | 14:1 (n-10) | 226.4 |
| cis-9-hexadecenoic | palmitoleic | 16:1 (n-7) | 254.4 |
| cis-6-octadecenoic | petroselinic | 18:1 (n-12) | 282.4 |
| cis-9-octadecenoic | oleic | 18:1 (n-9) | 282.4 |
| cis-11-octadecenoic | vaccenic (asclepic) | 18:1 (n-7) | 282.4 |
| cis-9-eicosenoic | Gadoleic | 20:1 (n-11) | 310.5 |
| cis-11-eicosenoic | Gondoic | 20:1 (n-9) | 310.5 |
| cis-11-docosenoic | Cetoleic | 22:1 (n-11) | 338.6 |
| cis-13-docosenoic | Erucic | 22:1 (n-9) | 338.6 |
| cis-15-tetracosenoic | Nervonic | 24:1 (n-9) | 366.6 |

Exemplary polyenoic fatty acids include those listed in the table below:

| Systematic name | Common name | Shorthand designation | Molecular wt. |
|---|---|---|---|
| 9,12-octadecadienoic | linoleic | 18:2 (n-6) | 280.4 |
| 6,9,12-octadecatrienoic | linolenic | 18:3 (n-6) | 278.4 |
| 8,11,14-eicosatrienoic | dihomolinolenic | 20:3 (n-6) | 306.5 |
| 5,8,11,14-eicosatetraenoic | arachidonic | 20:4 (n-6) | 304.5 |
| 7,10,13,16-docosatetraenoic | — | 22:4 (n-6) | 332.6 |
| 4,7,10,13,16-docosapentaenoic | — | 22:5 (n-6) | 330.6 |
| 9,12,15-octadecatrienoic | — | 18:3 (n-3) | 278.4 |
| 6,9,12,15-octadecatetraenoic | stearidonic | 18:4 (n-3) | 276.4 |
| 8,11,14,17-eicosatetraenoic | — | 20:4 (n-3) | 304.5 |
| 5,8,11,14,17-eicosapentaenoic | EPA | 20:5 (n-3) | 302.5 |
| 7,10,13,16,19-docosapentaenoic | DPA | 22:5 (n-3) | 330.6 |
| 4,7,10,13,16,19-docosahexaenoic | DHA | 22:6 (n-3) | 328.6 |
| 5,8,11-eicosatrienoic | Mead acid | 20:3 (n-9) | 306.5 |

In certain embodiments, the fatty acid used is oleic acid.

The amount of stabilizers in the emulsions of this invention may be, by charge ratio to the highly water-soluble drug, within a range of about 5:1 to about 3:1, about 2:1 to about 1:1, or 1.5:1 to 1:1.

As used herein, the term "emulsifiers" refers to compounds that allow the formation of a stable oil-in-water emulsion wherein the droplets are of sub-micron size and contain the highly water-soluble drug. Exemplary emulsifiers include compounds selected from phospholipids, bile salts, polyoxylene sorbitan fatty acid esters (e.g., TWEENS), polyoxyethylene castor oil derivatives (e.g., CREMOPHOR), albumin and poloxamer (e.g., PLURONIC), and mixtures thereof.

A "stable oil-in-water emulsion" refers to an oil-in-water emulsion wherein more than 50% of the oil droplets in the emulsion do not increase their size more than one-fold under appropriate storage conditions for at least 3 months.

In certain embodiments, the emulsion of the present invention is stable for at least 4, 5, 6, 7, 8, 9, 10, 11, 12, 14, 16, 18, 20, 22, or 24 months.

In certain embodiments, the average size of the oil droplets in the emulsion of the present invention does not increase by about 10%, 20%, 30%, 40%, 50%, 60%, 70%, 80%, 90%, 100%, 120%, 140%, 160%, 180%, 200%, or 250%.

In further embodiments, phospholipids may be used as emulsifiers. Phospholipids are available from naturally occurring sources or by organic synthesis. Lecithin is a naturally occurring mixture of the diglycerides of stearic, palmitic, and oleic acids, linked to the choline ester of phosphoric acid, commonly called phosphatidylcholine. Hydrogenated lecithin is the product of controlled hydrogenation of lecithin.

According to the United State Pharmacopoeia (USP), lecithin is a non-proprietary name describing a complex mixture of acetone-insoluble phospholipids, which consists primarily of phosphotidylcholine, phosphotidylethanolamine, phosphotidylserine and phosphotidylinositol, combined with various amounts of other substances such as triglycerides, fatty acids, and carbohydrates.

Pharmaceutically, lecithins are mainly used as dispersing, emulsifying, and stabilizing agents and are included in intramuscular and intravenous injections, parenteral nutritional formulations and topical products. Lecithin is also listed in the FDA Inactive Ingredients Guide for use in inhalations, intramuscular and intravenous injections, oral capsules, suspensions and tablets, rectal, topical, and vaginal preparations.

Phospholipids can also be synthesized and the common synthetic phospholipids are listed below:
Diacylglycerols
1,2-Dilauroyl-sn-glycerol (DLG)
1,2-Dimyristoyl-sn-glycerol (DMG)
1,2-Dipalmitoyl-sn-glycerol (DPG)
1,2-Distearoyl-sn-glycerol (DSG)
Phosphatidic Acids
1,2-Dimyristoyl-sn-glycero-3-phosphatidic acid, sodium salt (DMPA, Na)
1,2-Dipalmitoyl-sn-glycero-3-phosphatidic acid, sodium salt (DPPA, Na)
1,2-Distearoyl-sn-glycero-3-phosphatidic acid, sodium salt (DSPA, Na)
Phosphocholines
1,2-Dilauroyl-sn-glycero-3-phosphocholine (DLPC)
1,2-Dimyristoyl-sn-glycero-3-phosphocholine (DMPC)
1,2-Dipalmitoyl-sn-glycero-3-phosphocholine (DPPC)
1,2-Dipalmitoyl-sn-glycero-3-phosphocholine (DPPC)
1,2-Distearoyl-sn-glycero-3-phosphocholine (DSPC)
1,2-Distearoyl-sn-glycero-3-phosphocholine (DSPC)
Phosphoethanolamines
1,2-Dilauroyl-sn-glycero-3-phosphoethanolamine (DLPE)
1,2-Dimyristoyl-sn-glycero-3-phosphoethanolamine (DMPE)
1,2-Dipalmitoyl-sn-glycero-3-phosphoethanolamine (DPPE)
1,2-Distearoyl-sn-glycero-3-phosphoethanolamine (DSPE)
Phosphoglycerols
1,2-Dilauroyl-sn-glycero-3-phosphoglycerol, sodium salt (DLPG)
1,2-Dimyristoyl-sn-glycero-3-phosphoglycerol, sodium salt (DMPG)
1,2-Dimyristoyl-sn-glycero-3-phospho-sn-1-glycerol, ammonium salt (DMP-sn-1-G, NH4)
1,2-Dipalmitoyl-sn-glycero-3-phosphoglycerol, sodium salt (DPPG, Na)
1,2-Distearoyl-sn-glycero-3-phosphoglycerol, sodium salt (DSPG, Na)
1,2-Distearoyl-sn-glycero-3-phospho-sn-1-glycerol, sodium salt (DSP-sn-1 G, Na)
Phosphoserines
1,2-Dipalmitoyl-sn-glycero-3-phospho-L-serine, sodium salt (DPPS, Na)
Mixed Chain Phospholipids
1-Palmitoyl-2-oleoyl-sn-glycero-3-phosphocholine (POPC)
1-Palmitoyl-2-oleoyl-sn-glycero-3-phosphoglycerol, sodium salt (POPG, Na)

1-Palmitoyl-2-oleoyl-sn-glycero-3-phosphoglycerol, ammonium salt (POPG, NH4)
Lysophospholipids
1-Palmitoyl-2-lyso-sn-glycero-3-phosphocholine (P-lyso-PC)
1-Stearoyl-2-lyso-sn-glycero-3-phosphocholine (S-lyso-PC)
Pegylated Phospholipids
N-(Carbonyl-methoxypolyethyleneglycol 2000)-MPEG-2000-DPPE
1,2-dipalmitoyl-sn-glycero-3-phosphoethanolamine, sodium salt
N-(Carbonyl-methoxypolyethyleneglycol 5000)-MPEG-5000-DSPE
1,2-distearoyl-sn-glycero-3-phosphoethanolamine, sodium salt
N-(Carbonyl-methoxypolyethyleneglycol 5000)-MPEG-5000-DPPE
1,2-dipalmitoyl-sn-glycero-3-phosphoethanolamine, sodium salt
N-(Carbonyl-methoxypolyethyleneglycol 750)-MPEG-750-DSPE
1,2-distearoyl-sn-glycero-3-phosphoethanolamine, sodium salt
N-(Carbonyl-methoxypolyethyleneglycol 2000)-MPEG-2000-DSPE
1,2-distearoyl-sn-glycero-3-phosphoethanolamine, sodium salt In certain embodiments, the phospholipids in the formulations of the present invention may be egg or soy lecithin.

The amount of phospholipids, by weight, in the emulsions of the present invention may be within a range of about 2% to about 15%, such as at about 5% to about 10%.

As used herein, the term "bile salts" refers to salts of bile acid, i.e., steroids having 1-3 hydroxyl groups and a five-carbon atom side chain terminating in a carboxyl group, which can be conjugated to glycine or taurine. Bile salts include, but are not limited to, cholate, deoxycholate, chenodeoxycholate, or ursodeoxycholate, and their glycine or taurine conjugates, e.g., glycodeoxycholate (GDC), glycocholate (GC), or taurodeoxycholate (TDC).

As used herein, the term "preservatives" refers to agents that can prevent microbial growth in the emulsion formulation of this invention. The oil-in-water emulsions of this invention contain nutrients for microbes and may thus be conducive to microbial growth or contamination. Therefore, a preservative may be desirable in the formulation, especially for a vialed product that is intended to provide multiple doses where multiple punctures of the vial stopper by syringe needles are needed. The preservatives useful for this invention include, but are not limited to, sodium edetate (EDTA), sodium metabisulfite, sodium benzoate, benzyl alcohol, bronopol, parabens, cresol, phenol, phenoxyethanol, phenylmercuric acetate, phenylmercuric borate, phenylmercuric nitrate, sorbate, benzoate, sorbic acid thimerosal, cetrimide, chlorhexidine, chlorobutanol, chlorocresol, benzalkonium chloride and benzethonium chloride or a mixture thereof.

The other inactive ingredients used in the emulsion compositions of this invention may include virtually any component, such as an acid or base for pH adjustment such as hydrochloric acid and sodium hydroxide, agents to adjust the tonicity of the emulsion including sodium chloride, mannitol, sucrose, dextrose, lactose, polyethylene glycols (PEG) and glycerin or a mixture thereof.

The emulsion formulation of the present invention can be prepared so that it is ready-to-use or can be prepared with a cryoprotectant(s) as a lyophilized solid, i.e., "an oil-in-solid dispersion system" that can be reconstituted at a later date and diluted with water to reform the oil-in-water emulsion before injection.

As used herein, the term "an oil-in-solid dispersion system" refers to a solid matrix prepared by freeze-drying (lyophilizing) an oil-in-water emulsion of this invention and the solid matrix can reform an oil-in-water emulsion of similar droplet size upon mixing with water (reconstitution). In certain embodiments, the average droplet size of the reformed emulsion is no more than about 500%, 300%, or 150% of the average droplet size of the emulsion before the freeze-drying. An oil-in-solid dispersion system of this invention may be optionally prepared by spray drying.

"Cryoprotectants" used in the emulsion compositions of the present invention refers to those ingredients which are added to maintain the discrete and submicron droplets of the emulsion during the freeze-drying process and, upon the removal of aqueous phase of the emulsion, to provide a solid matrix for the droplets to form the an oil-in-solid dispersion system.

Cryoprotectants that may be used in the emulsion compositions of this invention include, but are not limited to, polyols, monosaccharides, disaccharides, polysaccharides, amino acids, peptides, proteins, and hydrophilic polymers, or mixtures thereof.

Polyols that may be used in the present invention include, but are not limited to, glycerin, mannitol, erythritol, maltitol, xylitol, sorbitol, polyglycitol or mixtures thereof.

Monosaccharides that may be used in this invention include, but are not limited to, glucose, mannose, fructose, lactulose, allose, altrose, gulose, idose, galactose, talose, ribose, arabinose, xylose, lyxose or mixtures thereof.

Disaccharides that may be used in this invention include, but are not limited to, sucrose, lactose, maltose, isomaltose, trehalose, cellubiose or mixtures thereof.

Polysaccharides that may be used in this invention include, but are not limited to, cellulose, amylose, inulin, chitin, chitosan, amylopectin, glycogen, pectin, hyaluronic acid or mixtures thereof.

Amino acids that may be used in this invention include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or mixtures thereof.

Peptides that may be used in this invention include, but are not limited to, diglycine and triglycine.

Proteins that may be used in this invention include, but are not limited to, albumin, collagen, casein, and gelatin.

Hydrophilic polymers that may be used in this invention include, but are not limited to, polyethylene glycols povidones, poloxamers, polyvinyl alcohols or mixtures thereof. The most preferred hydrophilic polymers are polyethylene glycols and povidones.

The concentration of the cryoprotectants used in the liquid emulsion compositions may be in the range of about 2% to about 40% w/w, such as about 5% to about 20% w/w and about 10% to about 15% w/w.

Generally, the emulsion formulation of the present invention can be prepared by performing one or more of the following steps:

(1) Dissolve the drug, triglyceride oil, emulsifier(s), and stabilizer(s) in a sufficient amount of a volatile solvent, such as ethanol, methylene chloride, chloroform, isopropanol, methanol, tert-butylalcohol, etc. to form a clear solution, (2) Remove the solvent to a toxicologically acceptable residual level by vacuum or by blowing solution with a nitrogen or air stream to obtain an oil phase.
(3) Dissolve the preservative(s), cryoprotectant(s), and other inactive ingredients in water to form an aqueous phase.
(4) Optionally filter the oil and/or aqueous phase to remove particles.
(5) Add the aqueous phase to the oil phase, and mix well to form a crude oil-in-water emulsion.
(6) Adjust pH of the crude emulsion to the desired pH range.
(7) Pass the crude emulsion through a high pressure homogenizer, such as a Microfluidizer 110F equipped with an emulsion interaction chamber by Microfluidics Corp, MA, operating at approximately 18000 psi pressure for 2 to 10 passages until the emulsion droplets reaches the desired average size range and the emulsion is free of droplets of greater than 5 microns in diameter.
(8) Aseptically pass the emulsion through a sterile 0.2 micron-rated membrane filter to sterilize the emulsion.
(9) Aseptically fill the filtered emulsion into appropriate sterile containers and seal the containers with appropriate sterile stoppers.
(10) Optionally the emulsions may be freeze-dried to form the oil-in-solid dispersion system.
(11) Perform necessary tests on the final emulsion or the oil-in-solid dispersion system.

The compositions of the present invention may be administered to an animal in need thereof via various routes, such as intravenous, intramuscular, intra-articular, intra-peritoneal, or oral administration.

The present invention also provides methods for using the compositions described herein. For instance, the present invention provides methods for treating cancer that comprise administering to a patient in need thereof compositions that comprise highly water soluble anti-neoplastic drugs (e.g., vinorelbine bitartrate).

The following examples are intended to illustrate the invention without limiting the practice thereof.

EXAMPLES

Example 1 pH-Stability Profiling of Vinorelbine in Selected pH Buffers

This study was to determine the range of pH in which vinorelbine is most stable. Vinorelbine solutions at 97.0 µg/mL concentrations were prepared at pH 1.95, 3.05, 5.98, 7.01 and 8.04 in sodium phosphate buffers, and at pH 4.01 and 5.01 in sodium acetate buffers.

The buffered venorelbine solutions were stored at 40° C. and analyzed by HPLC for vinorelbine concentrations at various time points. The recovery of vinorelbine over the initial concentration, representing the stability of vinorelbine in each buffer is shown in Table 1. The pH range in which vinorelbine is most stable was defined based on the maximum recovery.

TABLE 1

PH STABILITY STUDY OF VINORELBINE AT 97.0 µG/ML AT 40° C./75% RELATIVE HUMIDITY (RH) -% RECOVERY OVER 0 DAY TIME POINT

| Time point (day) | pH 1.95 | pH 3.04 | pH 4.01 | pH 5.01 | pH 5.98 | pH 7.01 | pH 8.04 |
|---|---|---|---|---|---|---|---|
| 3 | 97.9 | 99.9 | 98.2 | 97.5 | 97.9 | 96.1 | 92.1 |
| 7 | 97.3 | 99.7 | 100.4 | 98.6 | 105.0 | 94.8 | 88.0 |
| 14 | 90.2 | 98.1 | 97.0 | 97.6 | 96.9 | 91.4 | 85.1 |

Conclusion: vinorelbine appeared most stable at pH between 3 and 5, this acidic pH range was thus chosen for the emulsion formulations used in the other examples.

Example 2

Effect of Stabilizers on Vinorelbine Incorporation into the Oil Phase of an Emulsion Because of the high solubility of venorelbine in water, its incorporation in a normal oil phase was found minimal. In other words, without a stabilizer, venorelbine is present primarily in the aqueous phase.

The purpose of this study was to determine the effect of selected stabilizers on vinorelbine incorporation into the oil phase of an emulsion. Since venorelbine is a weak base, a stabilizer is preferred to be an acid with lipophilic property. Four stabilizers including sodium oleate, vitamin E succinate, riboflavin-5-phosphate sodium and cholesterol sulfate were evaluated. Each stabilizer contains an acid group head and a lipophilic tail, and is generally considered appropriate for injection.

Emulsions used for this study contained 1.4% (w/w) vinorelbine bitartrate, 10% (w/w) soybean oil, 1.2% (w/w) soy lecithin (Phospholipon® 90G by PHOSPHOLIPID GmbH), 0.005% (w/w) disodium EDTA, and 2.25% (w/w) glycerol. The concentration of each stabilizer added into formulation is: 1.57% (w/w) for sodium oleate, 2.73% (w/w) for vitamin E succinate, 2.46% (w/w) for riboflavin-5-phosphate sodium and 2.52% (w/w) for cholesterol sulfate. A formulation without any stabilizer ("control") and a formulation with extra Phospholipon 90G were also evaluated in the study.

The drug incorporation into the oil phase was tested using a dialysis method developed specifically for this purpose. This method involved filling 500 mg of an emulsion into a Slide-A-Lyzer dialysis cassette with 10,000 MW cutoffs, placing the cassette in 70 mL phosphate buffered saline (PBS), pH 7.4 and shaking the solution on a platform shaker at 100 RPM. A small volume (1 mL) of PBS was removed at each time point and analyzed by HPLC for vinorelbine concentration. The time profiles of vinorelbine concentration in PBS are shown in FIG. 1. The stabilizer that provided a high incorporation and small, uniform and stable emulsion droplets was selected as the preferred stabilizer for the emulsion formulations used in other examples.

Conclusion: The selected sterilizers were able to maintain vinorelbine in the oil droplets as demonstrated by significant reduction in the vinorelbine concentration in PBS, since the droplets are incapable of passing the dialysis membrane due to their size. Vitamin E succinate, sodium oleate and riboflavin-5-phosphate appeared to be the most effective stabilizers.

Example 3

Figure 2:
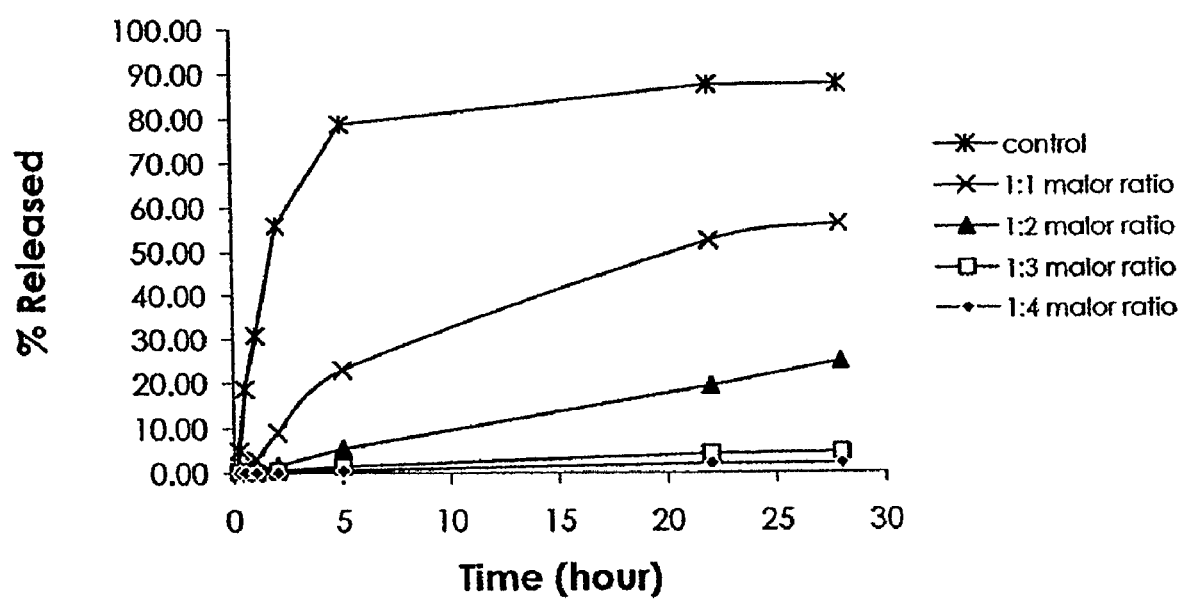
FIG. 2 shows the effects of concentrations of sodium oleate on the incorporation of vinorelbine into an emulsion.

Effect of Concentration of Sodium Oleate on the Incorporation of Vinorelbine into Emulsion Having determined sodium oleate being a strong stabilizer, emulsions of the same composition as in Example 2 were prepared with sodium oleate at 1.57% (w/w), 1.18% (w/w), 0.78% (w/w) or 0.39% (w/w), which correspond to a vinorelbine-to-oleate molar ratio of 1:4, 1:3, 1:2 or 1:1, or a charge ratio of 1:1, 1:0.75, 1:0.5 or 1:0.25, respectively. A dialysis test was performed under the same conditions as described in Example 2, and eight time points were taken for twenty-eight hours. PBS samples were analyzed by HPLC for vinorelbine concentration in phosphate buffered saline at each time point. The result is shown in FIG. 2. The optimal concentration of sodium oleate was determined based on the incorporation result and emulsion stability.

Conclusion: Sodium oleate added at a vinorelbine-to-oleate molar ratio of 1:4 (charge ratio of 1:1) almost completely stopped the partition of vinorelbine into the aqueous phase.

Example 4

Stability of Vinorelbine in Emulsions at a Neutral pH

Having determined the preferred stabilizer and stabilizer concentration, a preliminary emulsion was prepared and tested for short-term stability. The purpose of this study was to determine the possibility of a pH neutral emulsion based on vinorelbine stability. The emulsion prepared contained the following composition:

| | % (w/w) |
|---|---|
| Vinorelbine bitartarate | 1.389 (equivalent to 10 mg/mL vinorelbine freebase) |
| Soybean oil | 10 |
| Soy lecithin | 1.2 |
| Disodium EDTA dihydrate | 0.005 |
| Glycerol | 2.25 |
| Sodium oleate | 1.57 |
| Water QS to | 100 |
| pH | 7.4 |

Both physical and chemical stability of the emulsion were tested in this experiment. The physical stability was examined by measuring the average droplet size using laser light scattering spectrometry (Malvern zetasizer 3000) and by observing the gross and microscopic appearance of the emulsion. The chemical stability is represented by the vinorelbine stability and was examined by HPLC analysis.

TABLE 2

CHEMICAL STABILITY OF THE EMULSION AT PH 7.4

| Time point (day) | Storage condition | % Drug recovered over time 0 |
|---|---|---|
| 7 | −20° C. | 100.3 |
| | 25° C. | 92.4 |
| | 40° C. | 90.9 |
| 18 | −20° C. | 98.8 |
| | 25° C. | 93.0 |
| | 40° C. | 89.6 |

TABLE 3

PHYSICAL STABILITY OF THE EMULSION AT PH 7.4

| Time point (day) | Storage condition | Appearance | AVG droplet diameter (nm) | ≧5 micron droplets by microscopic examination |
|---|---|---|---|---|
| 0 | | Uniform | 179.2 ± 1.3 | None |
| 7 | −20° C. | | 7889.7 ± 3682.5 | Many |
| | 5° C. | Not uniform, some precipitate | 178.5 ± 1.3 | None |
| | 25° C. | Not uniform, some precipitate | 180.5 ± 2.0 | None |
| | 40° C. | Not uniform, some precipitate | 189.2 ± 2.2 | None |
| 18 | −20° C. | Phase separation | 2695.5 ± 2056.5 | Many |
| | 5° C. | Not uniform, some precipitate | 179.9 ± 0.4 | Some |
| | 25° C. | Uniform | 185.1 ± 2.8 | Many |
| | 40° C. | Uniform | 196.0 ± 0.6 | Many |

Conclusion: Vinorelbine emulsion at pH 7.4 is not stable both physically and chemically.

Example 5

Effect of Emulsion pH on Emulsion Uniformity and Droplet Size

After the pH-neutral emulsion (Example 4) failed to show satisfactory chemical stability, this study was performed to examine stability of emulsions at various pH (Example 1).

In addition, medium chain triglyceride (MCT) was added to replace 50% of the soybean oil. A brand product of MCT (Miglyol®812 by Sasol) was used. The addition of MCT was to improve the emulsion stability and reduce the droplet size. The combination of soybean oil and MCT at 1:1 ratio has been used in a number of IV fat emulsion product and thus was considered acceptable as a carrier for venorelbine.

The emulsion formulation contained:

| | % (w/w) |
|---|---|
| Venorelbine | 1.39 |
| Soybean oil | 5 |
| Miglyol 812N | 5 |
| Soy lecithin | 1.2 |
| Disodium EDTA dihydrate | 0.005 |
| Glycerol | 2.25 |
| Sodium oleate | 1.57 |
| Deionized water | QS | pH of the emulsions was adjusted to 7.03, 5.97, 4.97, 4.52, 3.95 and 3.74 using 0.5N HCl. The physical stability of these emulsions was examined and their appearance is summarized in Table 4. An emulsion with the most uniform in appearance and smallest and most stable droplet size was selected.

TABLE 4

PHYSICAL APPEARANCE OF EMULSIONS AT VARIOUS PH

| Emulsion pH | Filterability through 0.2 micron filters | AVG droplet diameter (nm) | Appearance |
|---|---|---|---|
| 7.03 | Easy | 169.8 ± 2.8 | Uniform |
| 5.97 | Didn't go through 0.2 μm | NA | Not uniform |
| 4.97 | Easy | 420.4 ± 8.3 | Not uniform |
| 4.52 | Easy | 471.9 ± 30.9 | Not uniform |
| 3.95 | Easy | 220.0 ± 1.0 | Not uniform |
| 3.74 | Easy | 191.1 ± 1.6 | Uniform |

Conclusion: Vinorelbine emulsions of uniform appearance and small droplet size (<200 nm) were only possible at pH 7.0 or pH 3.7.

Example 6 pH 3.7 Emulsion Stability

A portion of the pH 3.7 emulsion prepared in Example 5 was used to monitor the physical and chemical stability of the emulsion. The emulsion was aliquoted into 2 mL glass vial and stored at −20° C., 25° C. and 40° C. Up to 4-week stability results were generated (Tables 5 and 6).

TABLE 5

PHYSICAL STABILITY OF THE PH 3.74 EMULSION

| Time point (day) | Storage condition | AVG Droplet diameter (nm) | Appearance | Microscopic appearance |
|---|---|---|---|---|
| 7 | −20° C. | 121.4 ± 2.7 | Uniform | Uniform, No ≧5 micron droplets |
|  | 25° C. | 115.2 ± 0.7 | Uniform | Uniform, No ≧5 micron droplets |
|  | 40° C. | 123.6 ± 8.5 | Uniform | Uniform, Some ≧5 micron droplets |
| 14 | −20 | 149.0 ± 0.3 | Uniform | Uniform, Some ≧5 micron droplets |
|  | 25° C. | 112.8 ± 1.3 | Uniform | Uniform, No ≧5 micron droplets |
|  | 40° C. | 145.2 ± 2.6 | Uniform | Uniform, Some ≧5 micron droplets |
| 28 | −20° C. | NA | Not uniform | NA |
|  | 25° C. | 115.3 ± 5.3 | Uniform | Uniform, No ≧5 micron droplets |
|  | 40° C. | 113.2 ± 2.4 | Uniform | Uniform, some small particles |

TABLE 6

CHEMICAL STABILITY OF THE PH 3.75 EMULSION

| Time point (day) | Storage condition | Vinorelbine recovered (%) | Vinorelbine Purity (%) | RRT: 1.07-1.25 % Impurity#1 | % Impurity#2 |
|---|---|---|---|---|---|
| 7 | −20° C. |  | 98.4 | 0.93 | 0.92 |
|  | 25° C. | 101.8 | 98.0 | 0.68 | 1.64 |
|  | 40° C. | 99.8 | 97.9 | 1.21 | 1.14 |
| 14 | −20 |  | 98.5 | 0.74 | 0.68 |
|  | 25° C. | 101.1 | 98.5 | 0.69 | 0.67 |
|  | 40° C. | 98.2 | 97.8 | 0.91 | 1.06 |
| 28 | −20° C. |  | 97.8 | 0.91 | 1.78 |
|  | 25° C. | 98.5 | 98.1 | 1.03 | 0.79 |
|  | 40° C. | 95.7 | 96.6 | 1.92 | 1.99 |

Conclusion: The pH 3.7 vinorelbine emulsion appeared physically and chemically stable at 25° C.

Example 7

Dilution Study

This study was performed to determine the method by which the emulsion should be diluted for intravenous administration. Since the preferable emulsion is acidic, a neutralization and/or dilution step was tested for purpose of intravenous infusion.

The pH 3.7 liquid emulsion was diluted to 5.0 mg/mL vinorelbine freebase with 53 mM arginine freebase or 50 mM sodium hydroxide at a 1:1 volume ratio. The pH of the diluted/neutralized emulsion was 7.08 with 53 mM arginine and was 7.29 with 50 mM sodium hydroxide. The emulsions were further diluted to 0.5 mg/mL and 2 mg/mL vinorelbine freebase with 5% dextrose solution (D5W) for droplets stability monitoring at room temperature.

In another study, the pH 3.7 emulsion was diluted with D5W or lactated ringer's (LR) injection without arginine or sodium hydroxide as neutralizing agent. Again, the diluted emulsions were evaluated for droplets stability. The stability results of diluted emulsion are shown in Tables 7 and 8.

TABLE 7

EMULSION DROPLET SIZE UPON NEUTRALIZATION AND DILUTION

| Sample ID | Neutralize agent | Diluted with D5W to (mg/ml) | pH | ZAve (nm) at time 0 | ZAve (nm) at 7 hour |
|---|---|---|---|---|---|
| #1 | NaOH | 0.5 | 8.05 | 150.3 ± 5.1 | 181.4 ± 32.0 |
| #2 | NaOH | 2.0 | 7.70 | 138.9 ± 18.5 | 120.6 ± 3.5 |
| #3 | Arginine | 0.5 | 7.36 | 136.8 ± 5.9 | 212.6 ± 6.6 |
| #4 | Arginine | 2.0 | 7.29 | 138.9 ± 18.4 | 130.8 ± 10.0 |
| #5 | NA | Diluted with LR to 0.5 | 5.05 | 151.1 ± 10.8 | 265.5 ± 21.0 |
| #6 | NA | Diluted with LR to 2.0 | 4.68 | 136.7 ± 1.2 | 179.2 ± 26.7 |
| #7 | NA | Diluted with D5W to 0.5 | 4.11 | 124.3 ± 2.2 | 188.8 ± 0.9 |
| #8 | NA | Diluted with D5W to 2.0 | 3.73 | 185.4 ± 14.1 | 147.4 ± 10.3 |

TABLE 8

EMULSION APPEARANCE UPON NEUTRALIZATION AND DILUTION

| Sample ID | Neutralize agent | Diluted with D5W to (mg/ml) | pH | Microscope check at time 0 | Microscope check at 7 hour |
|---|---|---|---|---|---|
| #1 | NaOH | 0.5 | 8.05 | Some ≧5 micron droplets | Some ≧5 micron droplets |
| #2 | NaOH | 2.0 | 7.70 | Some ≧5 micron droplets | Some ≧5 micron droplets |
| #3 | Arginine | 0.5 | 7.36 | Some ≧5 micron droplets | Some ≧5 micron droplets |
| #4 | Arginine | 2.0 | 7.29 | Some ≧5 micron droplets | Some ≧5 micron droplets |
| #5 | NA | Diluted with LR to 0.5 | 5.05 | No ≧5 micron droplets | Some ≧5 micron droplets |
| #6 | NA | Diluted with LR to 2.0 | 4.68 | Some ≧5 micron droplets | Some ≧5 micron droplets |
| #7 | NA | Diluted with D5W to 0.5 | 4.11 | No ≧5 micron droplets | No ≧5 micron droplets |
| #8 | NA | Diluted with D5W to 2.0 | 3.73 | No ≧5 micron droplets | No ≧5 micron droplets |

Conclusion: The pH 3.7 vinorelbine emulsion of Example 5 may be diluted with D5W prior to intravenous infusion.

Example 8

Preparation of Vinorelbine Emulsion for Stability, Vein Irritation and Acute Toxicity Study In this example, an emulsion with the following composition was produced:

|  | % (w/w) |
|---|---|
| Vinorelbine bitartrate | 1.4 |
| Miglyol 812 N | 15 |
| Soy lecithin | 7.5 |
| Disodium EDTA dihydrate | 0.005 |
| Oleic acid | 1.5 |
| Sucrose | 15 |
| Deionized water to QS | 100 |
| HCl to adjust pH to | 3.5 +/− 0.2 |

The batch size was 108 mL. The following describes the method of preparation:

A. An oil phase was prepared by dissolving vinorelbine tartrate, Miglyol 812N, Soy lecithin, and oleic acid in a sufficient quantity of dehydrated ethanol to form a clear solution. The ethanol was removed using a Rotavapor (BÜCHI R-114) to a residual ethanol concentration of <1%.
B. An aqueous phase was prepared by dissolving sucrose and disodium EDTA dihydrate in water for Injection.
C. The oil and aqueous phases were mixed together using a Silverson homogenizer (Model L4RT with a 2" head) at 5,000-10,000 RPM for about 5 minutes to form a crude emulsion.
D. The pH of this crude emulsion was adjusted from 3.5 using 1N HCl.
E. The crude emulsion was homogenized for six passes in the Microfluidizer Model 110S.
F. In a laminar flow hood, the emulsion was filtered through a 0.45 μm filter and then a 0.2 μm sterile filter (Sartorius, MiniSart).
G. The filtered emulsion was dispensed in 5 mL aliquots into 5 mL pre-sterilized glass vials. These vials were sealed with pre-sterilized rubber stoppers.

Example 9

Stability of Vinorelbine Emulsion

The chemical stability of vinorelbine in the emulsion prepared in Example 8 was studied using reverse-phase HPLC method. This method allows determination of concentration and purity of vinorelbine in the emulsion. The vinorelbine chemical stability data of the emulsion are shown in the table below:

Chemical Stability

| Time point | Storage Condition | Conc. (μg/mL) | % Recovery | % Purity |
|---|---|---|---|---|
| 0 | NA | 14.0 | 100.0 | 98.5 |
| Wk 1 | −20° C. | 14.4 | 100.0 | 98.4 |
|  | 2-8° C. | 14.6 | 101.2 | 98.7 |
|  | 25° C. | 14.3 | 98.9 | 98.9 |
|  | 40° C. | 14.5 | 100.7 | 98.6 |
| Wk 2 | −20° C. | 14.3 | 100.0 | 99.0 |
|  | 2-8° C. | 13.9 | 97.5 | 99.3 |
|  | 25° C. | 14.1 | 98.6 | 98.9 |
|  | 40° C. | 14.2 | 99.5 | 98.5 |
| Wk 4 | −20° C. | 14.8 | 100.0 | 99.0 |
|  | 2-8° C. | 14.7 | 99.4 | 99.1 |
|  | 25° C. | 14.4 | 97.3 | 98.7 |
|  | 40° C. | 14.6 | 98.5 | 97.2 |
| Wk 12 | −20° C. | 14.0 | 100.0 | 99.1 |
|  | 2-8° C. | 14.0 | 100.1 | 99.1 |
|  | 25° C. | 14.3 | 102.7 | 99.0 |
|  | 40° C. | 13.7 | 98.2 | 98.9 |

The physical stability of the emulsion prepared in Example 8 was also evaluated. The physical stability was measured by the ability of the emulsion to maintain its average droplet size and the absence of large droplet (>5 micron in diameter). The average droplet size is determined by laser light scattering using a Malvern Zetasiziser 5000, and the presence of large droplet (>5 micron in diameter) was examined by observing the undiluted emulsion using an optical microscope at 400× magnifications. The physical stability data of the emulsion are provided in the table below:

Physical Stability

| Time point | Storage Condition | AVG Droplet size (nm) | Large droplets (>5 micron in diameter) | Visual appearance |
|---|---|---|---|---|
| 0 |  | 115 | None | Uniform |
| Wk 1 | −20° C. | 117 | Many | Uniform |
|  | 2-8° C. | 113 | None | Uniform |
|  | 25° C. | 120 | Some | Uniform |
|  | 40° C. | 146 | Some | Uniform |

-continued

| Time point | Storage Condition | AVG Droplet size (nm) | Large droplets (>5 micron in diameter) | Visual appearance |
|---|---|---|---|---|
| Wk 2 | −20° C. | 126 | Many | Uniform |
|  | 2-8° C. | 115 | None | Uniform |
|  | 25° C. | 122 | Some | Uniform |
|  | 40° C. | 162 | Many | Uniform |
| Wk 4 | −20° C. | 137 | Many | Uniform |
|  | 2-8° C. | 110 | Some | Uniform |
|  | 25° C. | 123 | Some | Uniform |
|  | 40° C. | 169 | Some | Uniform |
| Wk 12 | −20° C. | 201 | Many | N/A |
|  | 2-8° C. | 116 | None | Uniform |
|  | 25° C. | 143 | Some | Uniform |
|  | 40° C. | 117 | Some | Yellowish, viscous |

Conclusion: Vinorelbine is chemically stable in the emulsion prepared in Example 8 at 2-8° C. or 25° C., and the emulsion is physically stable at 2-8° C. for at least 12 weeks (3 months).

Example 10

Freeze-Drying Vinorelbine Emulsion

This study was to demonstrate the feasibility of converting a liquid emulsion to a freeze-dried emulsion or the "oil-in-solid dispersion system", which is believed more stable than the liquid emulsion.

Both low pH (pH 3.75) and neutral pH (pH 7.14) emulsion formulations were designed and prepared for freeze-drying or lyophilization study.

The formulation contained:

|  | % (w/w) |
|---|---|
| Vinorelbine bitartrate | 1.39 |
| Miglyol 812 N | 15 |
| Soy lecithin | 7.5 |
| Disodium EDTA dihydrate | 0.005 |
| Oleic acid | 1.45 |
| Sucrose | 15 |
| Deionized water to QS | 100 |

To prepare the freeze-dried emulsions, vinorelbine bitartrate, Miglyol 812, phospholipon 90G and oleic acid were first dissolved in sufficient amount of dehydrated ethanol to form a clear solution. The ethanol was removed using a rotary evaporator under vacuum at room temperature overnight to obtain an oil phase. The oil phase was mixed with an aqueous phase, which contained sucrose and sodium EDTA to form a crude emulsion using a high shear homogenizer. The oleic acid used in this formulation resulted in a low pH emulsion naturally. The crude emulsion was then microfluidized for 6 passages to form a pH 3.75 final emulsion.

A portion of the pH 3.75 crude emulsion was adjusted to pH 7.14 using 0.5N sodium hydroxide. The crude emulsion was then microfluidized for 6 passages to form a pH 7.14 final emulsion. Both emulsions were filtered through 0.2-micron filters and filled into as 1 mL each in 5 mL vials or 0.2 mL each in 2 mL vials. The height of the fill was about 3-4 mm. The vials were partially stoppered with lyophile stoppers and freeze-dried using a freeze-dryer (Dura-Stop™ mp by FTS System).

At the completion of the freeze-drying cycle, the freeze-dryer chamber was back filled with nitrogen gas NF to about 95% of atmospheric pressure and then fully stoppered by collapsing the shelves. The stoppered vials were sealed with aluminum crimp seals.

The dried emulsion or the oil-in-solid dispersion system was white "cakes" with uniform appearance. Prior to testing, the lyophile was reconstituted with deionized water and mixed for 1-2 minutes to re-form the liquid emulsion. The appearance (gross and microscopic) was recorded and the droplet size was determined (Table 9).

TABLE 9

VINORELBINE EMULSIONS PREPARED BY RECONSTITUTION OF THE OIL-IN-SOLID DISPERSION SYSTEM WITH DEIONIZED WATER

| Emulsion pH | Appearance | Microscopic appearance | Particle size (nm) |
|---|---|---|---|
| 3.75 | Uniform | No ≧5 micron droplets | 120.1 ± 3.0 |
| 7.14 | Not uniform | A lot of ≧5 micron droplets | NA |

Conclusion: The pH 3.7 vinorelbine emulsion may be freeze-dried to form the oil-in-solid dispersion system, and such oil-in-solid dispersion system can form an oil-in-water emulsion with size characteristics similar to the initial emulsion, upon dilution in water.

Example 11

Vein Irritation Test

The objective of this test is to compare vein irritation of a vinorelbine emulsion of the present invention with a marketed vinorelbine solution product. The vinorelbine emulsion used was prepared as in Example 8 (without the freeze-drying step). The marketed vinorelbine solution (MINNUOBIN® marketed by Sino-Sanofi in China) contains 1% vinorelbine tartrate (equivalent to 1% vinorelbine freebase) in water at pH 3.5. This product has the same composition as Navelbine®, which is marketed in the U.S by GlaxoSmithKline.

Six white rabbits were divided into three groups (two for each group, one male and one female). Each rabbit received daily an intravenous bolus injection through the marginal ear veins consecutively for 5 days. To Group I, 5% dextrose solution (D5W) was injected daily as a negative control.

To Group II, MINNUOBIN® was administered at a dose of 1.68 mg/kg/day after dilution to 0.3% vinorelbine freebases in D5W as a positive control.

To Group III, the vinorelbine emulsion prepared as in Example 8 was administered at a dose of 1.68 mg/kg/day either at 1% (undiluted) or after dilution to 0.3% vinorelbine freebase in D5W.

In Group III treated with the vinorelbine emulsion prepared as in Example 8, no drug-related signs of vein irritation were observed by appearance examination and pathology histology. All observed changes were due to mechanical punctuation during injection. Rabbits in Group II (treated with MINNUOBIN®) exhibited signs of mild to medium level vein irritation.

Conclusion: The vinorelbine emulsion of this invention did not cause vein irritation, while the solution formulation resulted in significant vein irritation at the same intravenous dose.

Example 12

Acute Toxicity Test

The objective of this test is to compare acute toxicity of a vinorelbine emulsion prepared as in Example 8 with a marketed vinorelbine solution product (MINNUOBIN®) in mice.

Mice (100) were divided into five (5) dose groups with 20 animals in each group (10 males and 10 females). MINNUOBIN® and the vinorelbine emulsion as described in Example 8 were administered intravenously. Immediate reactions were observed and acute toxicity was calculated using the Bliss method.

The iv×1 acute toxicity LD50 values were calculated as:

| | |
|---|---|
| Vinorelbine solution (MINNUOBIN ®): | 37.56 (34.24-41.21) mg/kg |
| Vinorelbine emulsion (Example 8): | 40.93 (37.75-44.38) mg/kg |

Conclusion: There was no statistical difference between these two groups.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for cancer chemotherapy that substantially avoids vein irritation, said method comprising:
    administering an oil-in-water emulsion to a cancer patient, wherein said oil-in-water emulsion comprises a vinorelbine salt and a fatty acid in about a 1:4 molar ratio of vinorelbine salt:fatty acid, wherein said vinorelbine salt is vinorelbine bitartrate and said fatty acid is oleic acid;
    wherein said vinorelbine salt is no less than 80% dissolved within the oil phase of said oil-in-water emulsion;
    wherein the formulation contains sucrose at about 15%; and
    wherein the formulation has a pH from about 3.5 to about 3.75, to thereby treat cancer and substantially avoid vein irritation.

2. The method of claim 1, wherein the oil-in-water emulsion further comprises a triglyceride oil and an emulsifier.

3. The method of claim 2, wherein the triglyceride oil is a triglyceride having long chain fatty acids, a triglyceride having medium chain fatty acids, or a mixture thereof.

4. The method of claim 2, wherein the triglyceride oil is a triglyceride having long chain fatty acids.

5. The method of claim 2, wherein the triglyceride oil is a triglyceride having medium chain fatty acids.

6. The method of claim 2, wherein the triglyceride oil is a mixture of triglyceride having long chain fatty acids and a triglyceride having medium chain fatty acids.

7. The method of claim 2, wherein the emulsifier is a member selected from the group consisting of egg lecithin, soy lecithin, a synthetic phospholipid, or a mixture thereof.

8. The method of claim 2, wherein the triglyceride oil is a 1:1 ratio of a medium chain triglyceride and a long chain triglyceride.

9. The method of claim 2, wherein the emulsifier is egg lecithin.

10. The method of claim 2, wherein the emulsifier is soy lecithin.

11. The method of claim 2, wherein the emulsifier is a synthetic phospholipid.

12. The method of claim 2, wherein the triglyceride is in a range of about 2% to about 40% w/w of the oil-in-water emulsion.

13. The method of claim 2, wherein the triglyceride is in a range of about 5%, 10%, 15%, 20%, 25%, 30%, or 35% w/w of the oil-in-water emulsion.

14. The method of claim 2, wherein the emulsifier is in a range of about 2% to about 15% of the oil-in-water emulsion.

15. The method of claim 1, wherein no less than 90% of vinorelbine is present in the oil phase of the emulsion.

16. The method of claim 1, wherein no less than 95% of the drug is present in the oil phase of the emulsion.

* * * * *